United States Patent
White et al.

(10) Patent No.: US 7,967,868 B2
(45) Date of Patent: Jun. 28, 2011

(54) PATIENT-MODIFIED IMPLANT AND ASSOCIATED METHOD

(75) Inventors: John R. White, Winona Lake, IN (US); Robert Metzger, Wakarusa, IN (US); Keith R. Berend, Columbus, OH (US)

(73) Assignee: Biomet Manufacturing Corp., Warsaw, IN (US)

( * ) Notice: Subject to any disclaimer, the term of this patent is extended or adjusted under 35 U.S.C. 154(b) by 256 days.

(21) Appl. No.: 12/103,834

(22) Filed: Apr. 16, 2008

(65) Prior Publication Data

US 2008/0262624 A1 Oct. 23, 2008

Related U.S. Application Data

(60) Provisional application No. 60/912,178, filed on Apr. 17, 2007.

(51) Int. Cl.
*A61F 2/38* (2006.01)

(52) U.S. Cl. .................... 623/20.35; 623/901

(58) Field of Classification Search ............. 623/16.11, 623/18.11, 20.14, 20.18–20.2, 20.35, 23.47, 623/901
See application file for complete search history.

(56) References Cited

U.S. PATENT DOCUMENTS

| | | |
|---|---|---|
| 4,436,684 A | 3/1984 | White |
| 4,506,393 A | 3/1985 | Murphy |
| 4,621,630 A | 11/1986 | Kenna |
| 4,632,111 A | 12/1986 | Roche |
| 4,663,720 A | 5/1987 | Duret et al. |
| 4,695,283 A | 9/1987 | Aldinger |
| 4,703,751 A | 11/1987 | Pohl |
| 4,704,686 A | 11/1987 | Aldinger |
| 4,721,104 A | 1/1988 | Kaufman et al. |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,007,936 A | 4/1991 | Woolson |

(Continued)

FOREIGN PATENT DOCUMENTS

CA 2447694 A1 12/2002

(Continued)

OTHER PUBLICATIONS

"Patient Matched PMI Implants, C.A.M.R.A. 3-D Imaging," brochure, Biomet, Inc. (1990) 6 pages.

(Continued)

*Primary Examiner* — Corrine M McDermott
*Assistant Examiner* — Megan Wolf
(74) *Attorney, Agent, or Firm* — Harness, Dickey (57) ABSTRACT

An orthopedic implant. The implant has a first portion including at least one patient-adjustable feature, and a second portion including at least one standard feature.

4 Claims, 4 Drawing Sheets

U.S. PATENT DOCUMENTS

| | | |
|---|---|---|
| 5,030,221 A | 7/1991 | Buechel et al. |
| 5,041,117 A | 8/1991 | Engelhardt |
| 5,053,039 A | 10/1991 | Hofmann et al. |
| 5,086,401 A | 2/1992 | Glassman et al. |
| 5,098,383 A | 3/1992 | Hemmy et al. |
| 5,129,908 A | 7/1992 | Petersen |
| 5,133,760 A | 7/1992 | Petersen et al. |
| 5,150,304 A | 9/1992 | Berchem et al. |
| 5,176,684 A | 1/1993 | Ferrante et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,408,409 A | 4/1995 | Glassman et al. |
| 5,440,496 A | 8/1995 | Andersson et al. |
| 5,448,489 A | 9/1995 | Reuben |
| 5,452,407 A | 9/1995 | Crook |
| 5,454,816 A | 10/1995 | Ashby |
| 5,496,324 A | 3/1996 | Barnes |
| 5,514,519 A | 5/1996 | Neckers |
| 5,527,317 A | 6/1996 | Ashby et al. |
| 5,539,649 A | 7/1996 | Walsh et al. |
| 5,554,190 A | 9/1996 | Draenert |
| 5,560,096 A * | 10/1996 | Stephens ........................ 29/558 |
| 5,571,110 A | 11/1996 | Matsen, III et al. |
| 5,607,431 A | 3/1997 | Dudasik et al. |
| 5,620,448 A | 4/1997 | Puddu |
| 5,634,927 A | 6/1997 | Houston et al. |
| 5,677,107 A | 10/1997 | Neckers |
| 5,681,354 A * | 10/1997 | Eckhoff ..................... 623/20.35 |
| 5,682,886 A | 11/1997 | Delp et al. |
| 5,690,635 A | 11/1997 | Matsen, III et al. |
| 5,702,460 A | 12/1997 | Carls et al. |
| 5,725,376 A | 3/1998 | Poirier |
| 5,725,593 A | 3/1998 | Caracciolo |
| 5,748,767 A | 5/1998 | Raab |
| 5,768,134 A | 6/1998 | Swaelens et al. |
| 5,792,143 A | 8/1998 | Samuelson et al. |
| 5,799,055 A | 8/1998 | Peshkin et al. |
| 5,871,018 A | 2/1999 | Delp et al. |
| 5,879,402 A | 3/1999 | Lawes et al. |
| 5,885,297 A | 3/1999 | Matsen, III |
| 5,885,298 A | 3/1999 | Herrington et al. |
| 5,901,060 A | 5/1999 | Schall et al. |
| 5,942,370 A | 8/1999 | Neckers |
| 5,967,777 A | 10/1999 | Klein et al. |
| 5,976,149 A | 11/1999 | Masini |
| 6,033,415 A | 3/2000 | Mittelstadt et al. |
| 6,126,690 A | 10/2000 | Ateshian et al. |
| 6,156,069 A | 12/2000 | Amstutz |
| 6,161,080 A | 12/2000 | Aouni-Ateshian et al. |
| 6,187,010 B1 | 2/2001 | Masini |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,343,987 B2 | 2/2002 | Hayama et al. |
| 6,383,228 B1 | 5/2002 | Schmotzer |
| 6,395,005 B1 | 5/2002 | Lovell |
| 6,427,698 B1 | 8/2002 | Yoon |
| 6,459,948 B1 | 10/2002 | Ateshian et al. |
| 6,463,351 B1 | 10/2002 | Clynch |
| 6,510,334 B1 | 1/2003 | Schuster et al. |
| 6,514,259 B2 | 2/2003 | Picard et al. |
| 6,558,391 B2 | 5/2003 | Axelson, Jr. et al. |
| 6,567,681 B1 | 5/2003 | Lindequist |
| 6,575,980 B1 | 6/2003 | Robie et al. |
| 6,591,581 B2 | 7/2003 | Schmieding |
| 6,696,073 B2 | 2/2004 | Boyce et al. |
| 6,701,174 B1 | 3/2004 | Krause et al. |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,740,092 B2 | 5/2004 | Lombardo et al. |
| 6,750,653 B1 | 6/2004 | Zou et al. |
| 6,772,026 B2 | 8/2004 | Bradbury et al. |
| 6,786,930 B2 | 9/2004 | Biscup |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,990,220 B2 | 1/2006 | Ellis et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,104,997 B2 | 9/2006 | Lionberger et al. |
| 7,141,053 B2 | 11/2006 | Rosa et al. |
| 7,198,628 B2 | 4/2007 | Ondrla et al. |
| 7,239,908 B1 | 7/2007 | Alexander et al. |
| 7,255,702 B2 | 8/2007 | Serra et al. |
| 7,282,054 B2 | 10/2007 | Steffensmeier et al. |
| 7,388,972 B2 | 6/2008 | Kitson |
| 7,468,075 B2 | 12/2008 | Lang et al. |
| 7,527,631 B2 | 5/2009 | Maroney et al. |
| 7,534,263 B2 | 5/2009 | Burdulis, Jr. et al. |
| 7,618,451 B2 | 11/2009 | Berez et al. |
| 2001/0005797 A1 | 6/2001 | Barlow et al. |
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2003/0039676 A1 | 2/2003 | Boyce et al. |
| 2003/0055502 A1 | 3/2003 | Lang et al. |
| 2003/0109784 A1 | 6/2003 | Loh et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0068187 A1 | 4/2004 | Krause et al. |
| 2004/0092932 A1 | 5/2004 | Aubin et al. |
| 2004/0102866 A1 | 5/2004 | Harris et al. |
| 2004/0106926 A1 | 6/2004 | Leitner et al. |
| 2004/0122439 A1 | 6/2004 | Dwyer et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0158254 A1 | 8/2004 | Eisermann |
| 2004/0171924 A1 | 9/2004 | Mire et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0243481 A1* | 12/2004 | Bradbury et al. ............... 705/26 |
| 2004/0254584 A1 | 12/2004 | Sarin et al. |
| 2005/0008887 A1 | 1/2005 | Haymann et al. |
| 2005/0049524 A1 | 3/2005 | Lefevre et al. |
| 2005/0059873 A1 | 3/2005 | Glozman et al. |
| 2005/0065628 A1 | 3/2005 | Roose |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0148843 A1 | 7/2005 | Roose |
| 2005/0171545 A1 | 8/2005 | Walsh et al. |
| 2005/0203536 A1 | 9/2005 | Laffargue et al. |
| 2005/0234461 A1 | 10/2005 | Burdulis et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0267584 A1 | 12/2005 | Burdulis et al. |
| 2006/0004284 A1 | 1/2006 | Grunschlager et al. |
| 2006/0030853 A1 | 2/2006 | Haines |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0089621 A1 | 4/2006 | Fard |
| 2006/0094951 A1 | 5/2006 | Dean et al. |

| | | |
|---|---|---|
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0161167 A1 | 7/2006 | Myers et al. |
| 2006/0172263 A1 | 8/2006 | Quadling et al. |
| 2006/0190086 A1* | 8/2006 | Clemow et al. ............ 623/20.15 |
| 2006/0204932 A1 | 9/2006 | Haymann et al. |
| 2006/0271058 A1 | 11/2006 | Ashton et al. |
| 2006/0276796 A1 | 12/2006 | Creger et al. |
| 2006/0287733 A1 | 12/2006 | Bonutti |
| 2007/0015995 A1 | 1/2007 | Lang et al. |
| 2007/0016209 A1 | 1/2007 | Ammann et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0156171 A1 | 7/2007 | Lang et al. |
| 2007/0185498 A2 | 8/2007 | Lavallee |
| 2007/0198022 A1 | 8/2007 | Lang et al. |
| 2007/0203605 A1 | 8/2007 | Melton et al. |
| 2007/0219639 A1 | 9/2007 | Otto et al. |
| 2007/0226986 A1 | 10/2007 | Park et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0250169 A1 | 10/2007 | Lang |
| 2007/0276224 A1 | 11/2007 | Lang et al. |
| 2007/0276400 A1 | 11/2007 | Moore et al. |
| 2007/0288030 A1 | 12/2007 | Metzger et al. |
| 2008/0009952 A1 | 1/2008 | Hodge |
| 2008/0015605 A1 | 1/2008 | Collazo |
| 2008/0021299 A1 | 1/2008 | Meulink |
| 2008/0021567 A1 | 1/2008 | Meulink et al. |
| 2008/0051910 A1 | 2/2008 | Kammerzell et al. |
| 2008/0114370 A1 | 5/2008 | Schoenefeld |
| 2008/0146969 A1 | 6/2008 | Kurtz |
| 2008/0147072 A1 | 6/2008 | Park et al. |
| 2008/0161815 A1 | 7/2008 | Schoenefeld et al. |
| 2008/0195107 A1 | 8/2008 | Cuckler et al. |
| 2008/0195216 A1 | 8/2008 | Philipp |
| 2008/0243127 A1 | 10/2008 | Lang et al. |
| 2008/0257363 A1 | 10/2008 | Schoenefeld et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2008/0312659 A1 | 12/2008 | Metzger et al. |
| 2008/0319448 A1* | 12/2008 | Lavallee et al. ............... 606/102 |
| 2009/0018546 A1 | 1/2009 | Daley |
| 2009/0024131 A1 | 1/2009 | Metzger et al. |
| 2009/0076512 A1 | 3/2009 | Ammann et al. |
| 2009/0089034 A1 | 4/2009 | Penney et al. |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0131941 A1 | 5/2009 | Park et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0187193 A1 | 7/2009 | Maroney et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0228016 A1 | 9/2009 | Alvarez et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2010/0016986 A1 | 1/2010 | Trabish |
| 2010/0030231 A1 | 2/2010 | Revie et al. |

FOREIGN PATENT DOCUMENTS

| | | |
|---|---|---|
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| EP | 0114505 A1 | 8/1984 |
| EP | 0326768 A2 | 8/1989 |
| EP | 1321107 A1 | 6/2003 |
| EP | 1437102 A1 * | 7/2004 |
| EP | 01486900 A1 | 12/2004 |
| FR | 2659226 A1 | 9/1991 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9959106 A1 | 11/1999 |
| WO | WO-0170142 A1 | 9/2001 |
| WO | WO-0184479 A1 | 11/2001 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2005051239 A1 | 6/2005 |
| WO | WO-2005051240 A1 | 6/2005 |
| WO | WO-2006058057 A2 | 6/2006 |
| WO | WO-2006060795 A1 | 6/2006 |
| WO | WO-2006127486 A2 | 11/2006 |
| WO | WO-2006134345 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007145937 A2 | 12/2007 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008112996 A1 | 9/2008 |

OTHER PUBLICATIONS

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Charl P., Technical Report: DeVIDE—The Delft Visualisation and Image processing Development Environment, pp. 1-49 (May 31, 2006).

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazan, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability for PCT/US2007/013223 issued Nov. 26, 2007.

International Search Report and Written Opinion for PCT/US2007/013223 mailed Nov. 26, 2007.

International Search Report and Written Opinion for PCT/US2009/039507 mailed Jul. 14, 2009.

International Search Report and Written Opinion for PCT/US2009/039578 mailed Jul. 31, 2009.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Klein, M., "Robot assisted insertion of craniofacial implants—clinical experience," CARS 2001, pp. 133-138 (2001) Elsevier Science B.V.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).

International Search Report and Written Opinion mailed Apr. 22, 2010 for PCT/US2010/024579 claiming benefit of U.S. Appl. No. 12/389,930, filed Feb. 20, 2009.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

* cited by examiner

PATIENT-MODIFIED IMPLANT AND ASSOCIATED METHOD

CROSS-REFERENCE TO RELATED APPLICATIONS

This application claims the benefit of U.S. Provisional Application No. 60/912,178, filed on Apr. 17, 2007.

This application is related to U.S. application Ser. No. 11/756,057, filed on May 31, 2007, which claims the benefit of U.S. Provisional Application No. 60/812,694, filed on Jun. 9, 2006.

The disclosures of the above applications are incorporated herein by reference.

INTRODUCTION

Various custom made, patient-specific orthopedic implants and associated templates and guides are known in the art. Such implants and guides can be developed using commercially available software. Custom guides are used to accurately place pins, guide bone cuts, and insert implants during orthopedic procedures. The guides are made from a preoperative plan formed from an MRI or CT scan of the patient and rely on matching an anatomic feature for correct positioning.

The present teachings provide semi-custom implants that can reduce inventory and allow more accurate placement and additional flexibility in addressing diverse patient-specific requirements.

SUMMARY

The present teachings provide an orthopedic implant. The implant has a first portion including at least one patient-adjustable feature, and a second portion including at least one standard feature.

The present teachings also provide an orthopedic implant manufacturing method. The method includes preparing a three-dimensional image of a patient's joint, selecting a standard size implant closely matching the joint, and modifying at least one feature of the implant to be patient-specific.

In another aspect, the implant is a femoral implant, and the method includes modifying a plurality of features of the femoral implant to be patient-specific.

Further areas of applicability of the present teachings will become apparent from the description provided hereinafter. It should be understood that the description and specific examples are intended for purposes of illustration only and are not intended to limit the scope of the teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the teachings, its application, or uses. For example, although the present teachings are illustrated for specific implants and alignment guides in hip or knee surgery, the present teachings can be used with other implants and guides, templates, jigs, drills, rasps or other instruments used in various orthopedic procedures.

The present teachings generally provide a surgery system for use in orthopedic surgery for the knee, hip, or shoulder, for example. The surgery system can include various implant components 100, patient-specific alignment guides or templates 600, and cutting blocks or other conventional instruments 610, 620 that can be used in the specific orthopedic procedure. At least one implant component 100 can be semi-custom made. The semi-custom implant components are standard size components that have at least one feature modified to match a specific patient, as discussed below.

The alignment guides 600 can be used either with conventional (standard size) or patient-specific femoral and tibial prosthesis components prepared with computer-assisted image methods. The implant components 100 can be patient-specific (custom made) or semi-custom. Computer modeling for obtaining three dimensional images of the patient's anatomy using MRI or CT scans of the patient's anatomy, the semi-custom and/or custom made implant components 100, and the patient-specific alignment guides 600 can be provided by various CAD programs and/or software available, for example, by Materialise USA, Ann Arbor, Mich.

The alignment guides 600 can be generally formed using computer modeling for matching a three-dimensional image of the patient's bone surface (with or without the cartilage) by known methods. Further details of patient-specific alignment guides and associated methods are disclosed in U.S. application Ser. No. 11/756,057, filed on May 31, 2007, the disclosure of which is incorporated herein by reference.

Similarly, the implant components can be selected and modified to include patient-specific features by using computer modeling of the joint, as described above. A set of conventional femoral knee implants can be modeled and overlaid over the CAD image data to first determine the closest fit based on standard sizes. These standard sized overlays or templates can be based on commercially available implant systems, such as, for example, the Vanguard Knee System, commercially available from Biomet, Inc, of Warsaw, Ind., in size increments of 2.5 mm. Using standard sized implants as a base for semi-custom implant components can allow standard instrument sets to be used depending on the specific size selected. After the overlay is positioned on the digital representation of the femur, various adjustments can be made to this femoral implant.

Figure 1:
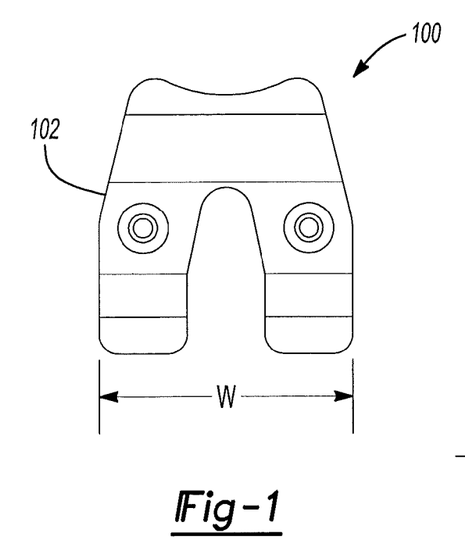
FIG. 1 is a plan view of an exemplary femoral implant according to the present teachings.
Figure 2:
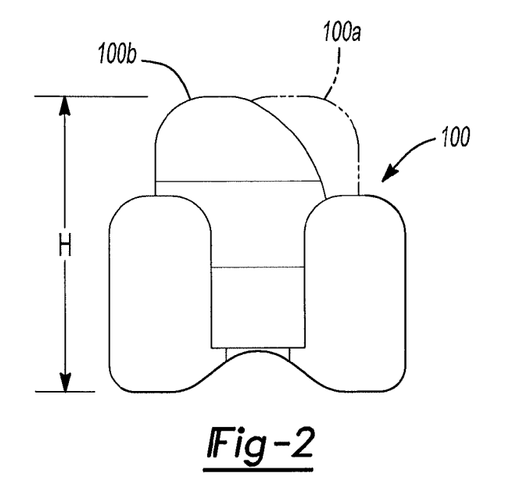
FIG. 2 is a posterior elevated view of the femoral implant of FIG. 1.
Figure 3:
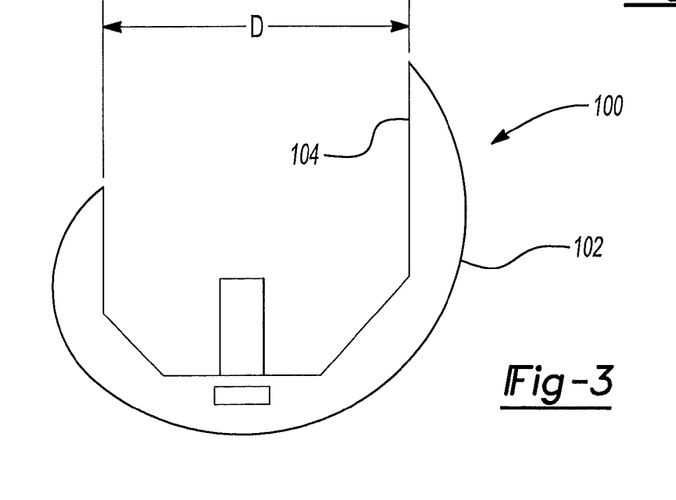
FIG. 3 is an anterior-posterior sectional view of the femoral implant of FIG. 1.

Referring to FIGS. 1-3, various views of an exemplary semi-custom implant component 100 in the form of a femoral component for a knee replacement surgery system are illustrated. The semi-custom implant component 100 can include certain portions that are custom-made to match a particular patient using imaging techniques, and other portions that are provided in a series of standardized size increments to ensure a good fit. For example, the outside geometry of the femoral component 100 can be patient-specific or patient-matched. As an illustration, the width W and height H, and/or optionally the shape and dimensions of the entire articulating or outer surface 102, or portions thereof, can match/conform with that of the patient's corresponding joint surface. The inside geometry of the femoral component 100, such as the bone-engaging inner surface 104, can be selected from a standardized series of sizes, thereby allowing the use of standard instruments, such as cutting guides and resection instruments, to be used with the semi-custom implant components 100, and avoiding the need for specialized instruments and associated manufacturing and training costs.

With continued reference to FIGS. 1-3, to obtain a good match, the difference between consecutive sizes in the inner anterior-posterior distance D can be 3 mm or less to allow for as good a fit between the implant component 100 and the joint surface without the need to match or conform the inner surface 104 to the patient. In other words, the semi-custom implant component 100 is an implant component that can include certain portions, including shapes, dimensions, and/or sizes that are custom-made for a particular patient, while other portions including shapes and/or dimensions of the component are provided in a series of standardized sizes in increments that can provide a good fit without being fully custom-made to a particular patient.

Figure 8:
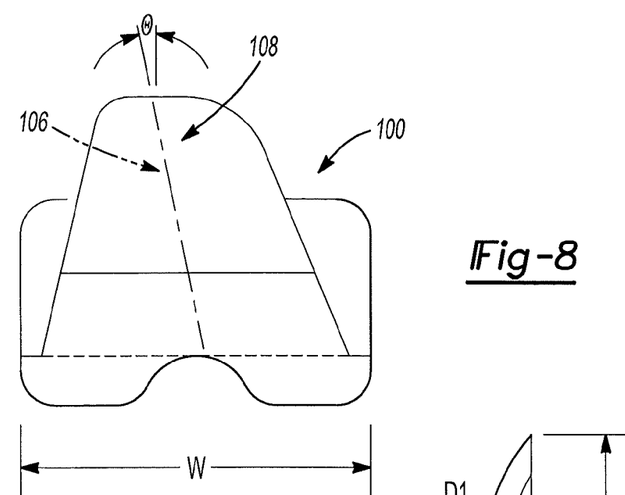
FIG. 8 is an anterior elevated view of a femoral implant according to the present teachings.
Figure 9:
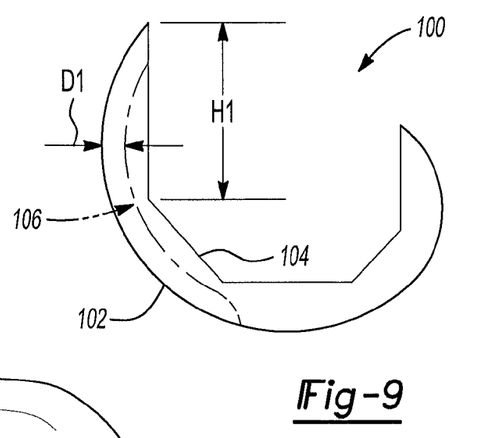
FIG. 9 is an anterior-posterior sectional view of the femoral implant of FIG. 8.

In another aspect, and referring to the exemplary illustrations of FIGS. 8 and 9, five adjustments can be made to a standard size femoral component to obtain a semi-custom femoral implant component 100. These five adjustments can include the medial/lateral width W, the angle θ of the patella track 106, the depth D1 of the patella track, the shape of the anterior flange 108, such as right or left-sided and a height of the anterior flange, such as the height H1 shown in FIG. 9, or overall height H, shown in FIG. 2. These five features or parameters can be adjusted to more closely match the knee of the patient without requiring changes in the standard cuts for the selected standard knee implant, because the bone engaging inner surface 104 does not substantially change allowing standard cutting guides and resections instruments corresponding to standard sizes to be used. This modified or patient matched digital model of the semi-custom implant can then be provided to the surgeon along with the image data for review. The surgeon can confirm whether the proposed design is acceptable, and the specific patient matched implant can be manufactured from the digital model.

Figure 10:
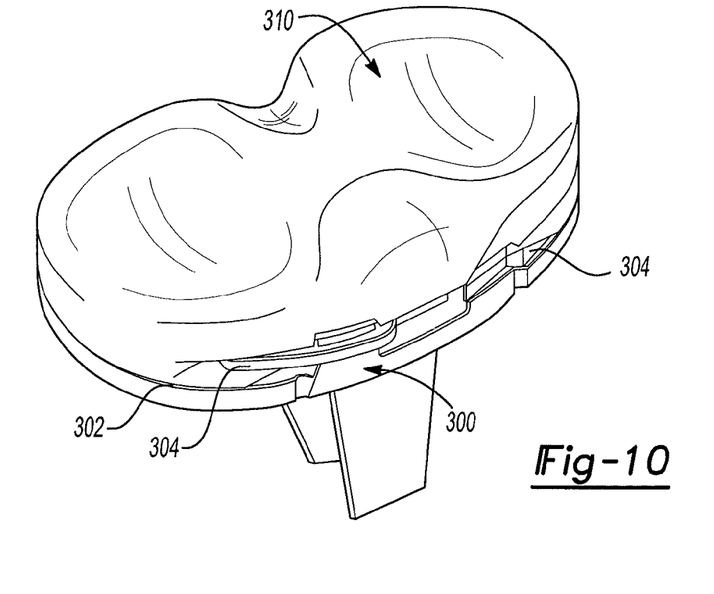
FIG. 10 is a perspective view of a tibial component according to the present teachings.

The surgery system can include patient-specific and/or conventional (standard size) implants for the remaining components of the knee replacement system, such as the tibial component, bearing component and patella component. For example, and referring to FIG. 10, a tibial component 300 can be designed with a profile 302 that matches and conforms to the patient's anatomy based on the 3-D image data of the patient's bone. The resulting tibial component 300 can still have standard features, including a standard locking mechanism for bearings, such as, for example, slots 304 for coupling with a standard bearing component 310. The standard locking mechanism allows existing inventory of bearings to be used. In another aspect, the bearing components 310 can be similarly customized.

In another aspect, the tibial component 300 can also be designed in closely packed tibial sizes that very in increments of less that 2 mm in width and are available for manufacture on as-needed basis. When used with patient-specific alignment guides made from digital images of the joint, the closely packed sizes need not be stocked in inventory, but manufactured only in the size determined from the digital image from planned molds or other just-in-time manufacturing methods.

In another aspect, disease-specific off-the shelf implants can be provided and included in a surgery kit. Each disease-specific implant can be designed to address a specific deformity, by making angle or size adjustment related to the deformity, such as different lengths or thickness or angles of certain portions of the implant component, such as the size and shape of femoral condyles, the patella track angle, etc. Each disease-specific implant can be used for multiple patients with the same deformity/disease, such as valgus, varus or flexion deformities. In this regard, for each patient with the same deformity, one or more off-the-shelf disease-specific implants can be selected to address the patient's needs without using patient-specific implants.

Figure 4:
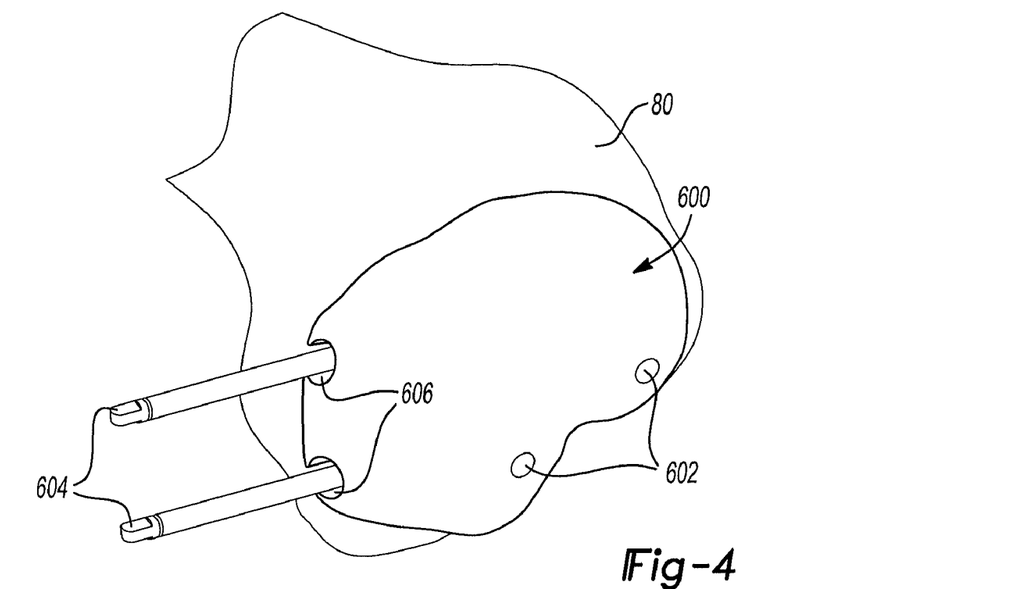
FIG. 4 is an environmental view illustrating an exemplary femoral alignment guide according to the present teachings.
Figure 5:
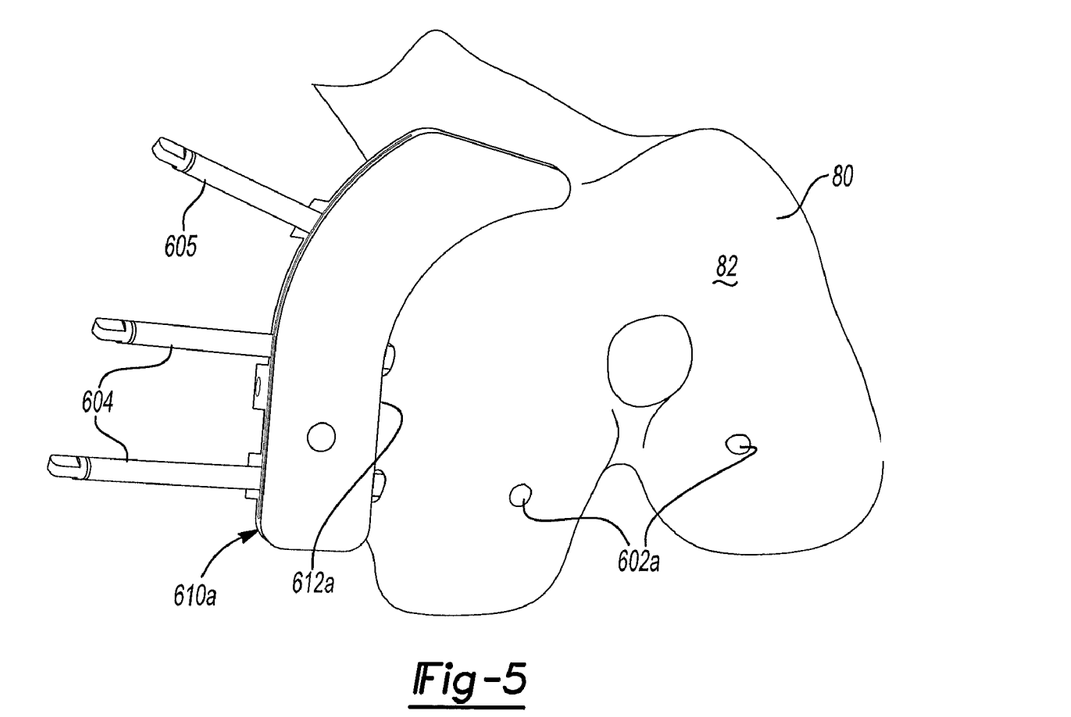
FIG. 5 is an environmental view illustrating an exemplary distal cutting block according to the present teachings.
Figure 6:
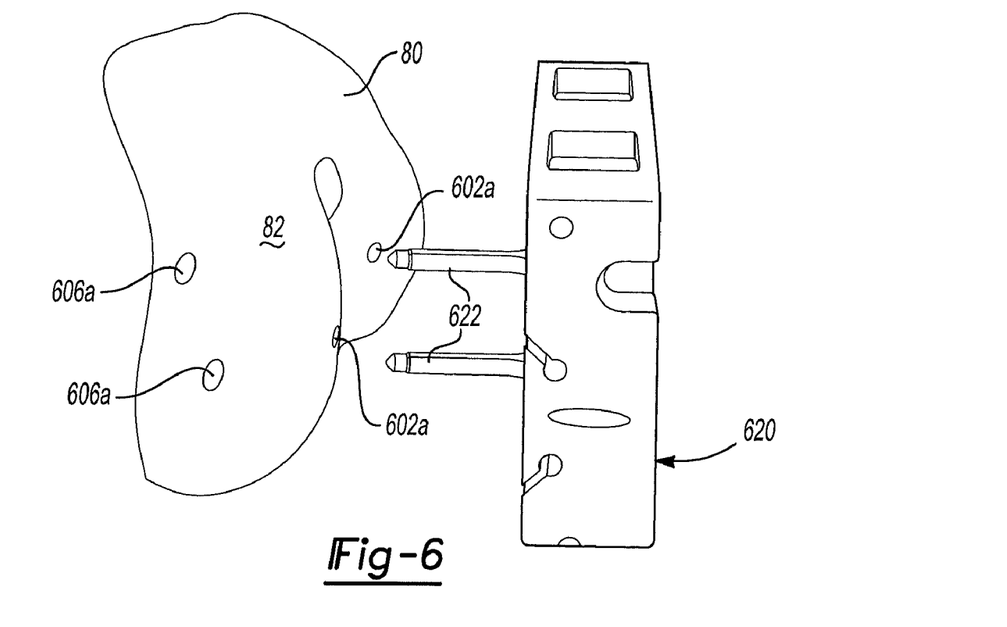
FIG. 6 is an environmental view illustrating an exemplary four-in-one cutting block according to the present teachings.

The surgery system can also include patient-specific alignment guides 600, as illustrated in FIG. 4 for a joint surface 82 of the distal femur 80. The patient specific alignment guide 600 can define openings 606 for guide elements 604 that pass through corresponding holes 606a drilled in the femur, and openings 602 for drilling holes 602a on the femur 80, as shown in FIGS. 4, and 6. The surgery system can also include a set of cutting blocks for the femoral joint surface 82, such as the distal cutting block 610 illustrated in FIG. 5 and mounted on the femur 80 with various guide or fixation elements 604, 605, and the four-in-one cutting block 620 illustrated in FIG. 6. The four-in-one cutting block 620 can be supported on the femur with pins 622 received in openings 602a. Other cutting blocks, drill guides or other instruments can also be used. The joint surface 82 can be a bone surface with or without soft tissue, such as articular cartilage for the knee or other joint soft tissue. It will be appreciated that other instruments, such as drill guides, guide pins, attachment pins or pegs or others can be included in the surgery system.

Figure 7:
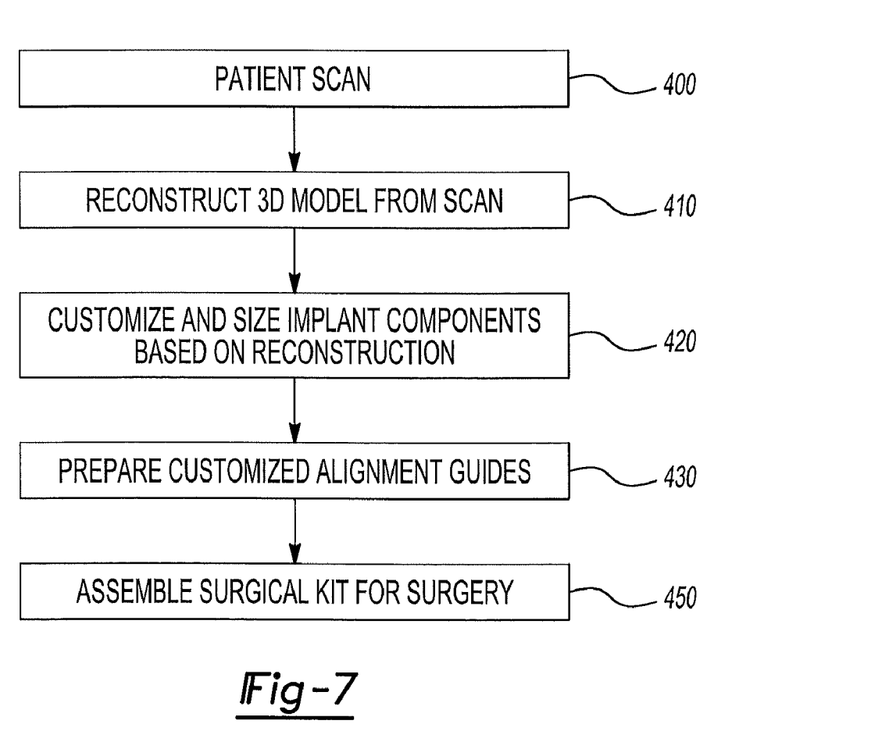
FIG. 7 is a flowchart of an exemplary method according to the present teachings.

The surgery system can be used for surgical pre-planning as illustrated in FIG. 7. The patient's knee, or other joint, can be scanned using an imaging technique, such as MRI or CT, at 400. A three-dimensional (3D) model of the joint surfaces can be reconstructed at 410 using known computer imaging methods. The implant components 100 can be designed, sized and positioned using the 3D reconstruction, at 420. As discussed above, the implant components 100 can include conventional, custom made, or semi-custom implant components 100. The semi-custom implant components can include some portions that are of standard sizes, such as the bone-engaging inner surface 104, and other portions that are customized for the patient, including portions of the articulating surface or other outer dimensions and orientations of the articulating surface 102 of the implant 100. Customized alignment guides 600 for the joint surfaces, such as femoral and tibial alignment guides 600 for a total knee replacement, can be designed and prepared based on the 3D reconstruction and the implants 100, at 430. A surgery system or kit can be assembled for the surgeon at the time of surgery, at 450. The surgery system can include at least one semi-custom implant component 100, at least one patient specific alignment guide 600, and at least one cutting block 610.

It will be appreciated that surgery kits as described above can be constructed for various joints, including the knee, the hip, the shoulder, etc. The present teachings provide the ability to customize implant and alignment guide components and their position using patient-specific data. Further, the amount of inventory required in the operating room can be reduced because the sizes of the various semi-custom implant components 100 are known prior to surgery and only the required size is sent to the surgeon for the surgical procedure. In another aspect, when close-packed sizes are planned, the small difference between individual sizes of the implant components 100, such as 3 mm or 2.5 mm or less, can allow optimal anterior-posterior fit to the joint surface 80 without adverse impact on inventory requirements, because only the required size can be manufactured and shipped for a specific patient based on the patient's image data. Additionally, the use of semi-custom implant components based on anterior-posterior sizing, as contrasted to fully patient-specific components, allows use and re-use of standard cutting blocks. Disposable cutting blocks can also be mass produced in high volumes at less cost because of the standardization.

The foregoing discussion discloses and describes merely exemplary arrangements of the present teachings. One skilled in the art will readily recognize from such discussion, and from the accompanying drawings that various changes, modifications and variations can be made therein without departing from the spirit and scope of the teachings as described herein.

What is claimed is:

1. An orthopedic implant manufacturing method comprising:
    preparing a three-dimensional digital image of a patient's joint using computer modeling;
    creating a digital image of a non patient-specific femoral implant selected to closely match a size of the patient's joint, the implant having an inner bone engaging surface including a plurality of planar surfaces for engagement with corresponding standard size non-patient specific bone cuts;
    overlaying the digital image of the implant on the image of the patient's joint;
    modifying a shape of an anterior flange of the digital image of the femoral implant to be patient-matched and closely match a corresponding feature of the three-dimensional image of the patient's joint without modifying the planar surfaces of the inner bone engaging surface; and
    manufacturing a patient-matched implant from the digital image of the femoral implant as modified.

2. An orthopedic implant manufacturing method comprising:
    preparing a three-dimensional digital image of a patient's joint using computer modeling;
    creating a digital image of a non patient-specific femoral implant selected to closely match a size of the patient's joint, the implant having an inner bone engaging surface including a plurality of planar surfaces for engagement with corresponding standard size non-patient specific bone cuts;
    overlaying the digital image of the implant on the image of the patient's joint;
    modifying an orientation of a patella track of the digital image of the femoral implant to be patient-matched and closely match a corresponding feature of the three-dimensional image of the patient's joint without modifying the planar surfaces of the inner bone engaging surface; and
    manufacturing a patient-matched femoral implant from the digital image of the femoral implant as modified.

3. An orthopedic implant manufacturing method comprising:
    preparing a three-dimensional digital image of a patient's joint using computer modeling;
    creating a digital image of a non patient-specific femoral implant selected to closely match a size of the patient's joint, the femoral implant having an inner bone engaging surface including a plurality of planar surfaces for engagement with corresponding standard size non-patient specific bone cuts;
    overlaying the digital image of the implant on the image of the patient's joint;
    modifying a depth of a patella track of the digital image of the femoral implant to be patient-matched and closely match a corresponding feature of the three-dimensional image of the patient's joint without modifying the planar surfaces of the inner bone engaging surface; and
    manufacturing a patient-matched femoral implant from the digital image of the femoral implant as modified.

4. The method of claim 3, further comprising manufacturing a patient-specific alignment guide for the joint based on the three-dimensional image of the patient's joint.

* * * * *